(12) United States Patent
Sharma (10) Patent No.: US 7,515,261 B2
(45) Date of Patent: Apr. 7, 2009

(54) CAPILLARY BASED OPTICAL MEASUREMENT SYSTEM

(75) Inventor: Manish Sharma, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 60 days.

(21) Appl. No.: 11/368,968

(22) Filed: Mar. 6, 2006

(65) Prior Publication Data

US 2007/0206186 A1 Sep. 6, 2007

(51) Int. Cl.
*G01J 3/30* (2006.01)
(52) U.S. Cl. .................................... 356/317
(58) Field of Classification Search ............... 356/317, 356/338
See application file for complete search history.

(56) References Cited

U.S. PATENT DOCUMENTS

| | | | |
|---|---|---|---|
| 4,462,962 A * | 7/1984 | Baba et al. ................ 422/58 |
| 4,690,560 A | 9/1987 | Coogan | |
| 4,726,681 A * | 2/1988 | Webb ....................... 356/338 |
| 6,104,485 A | 8/2000 | Wang et al. | |
| 6,426,615 B1 | 7/2002 | Mehta | |
| 6,826,422 B1 * | 11/2004 | Modell et al. ............. 600/407 |
| 6,906,797 B1 * | 6/2005 | Kao et al. ................. 356/317 |
| 6,974,673 B2 * | 12/2005 | Lockhart .................. 435/7.1 |
| 2006/0146327 A1 * | 7/2006 | Wang et al. .............. 356/338 |

* cited by examiner

*Primary Examiner*—Kara E Geisel
*Assistant Examiner*—Abdullahi Nur (57) ABSTRACT

Provided is a system for characterizing biological/chemical test specimens. In particular, a container such as a tube or capillary for containing a test specimen is interconnected at one end to a light source via a fiber optic. A second end of the tube is connected to a detector via a second fiber optic. In one embodiment, the containing tube exhibits "total internal reflection". As light is projected into the tube, one or more electric fields are applied to the specimen. Light travels the length of the tube to excite specimen molecules, which subsequently emit light having a wavelength longer than that of the projected light. The emitted light travels the length of the tube, is detected, and is then transmitted to a processor for analysis. In an alternate embodiment, the tube is not TIR therefore emitted light exits the tube along its length, wherein it is detected by one or more detectors.

26 Claims, 4 Drawing Sheets

CAPILLARY BASED OPTICAL MEASUREMENT SYSTEM

FIELD

This invention relates generally to the field of fluorescence spectroscopy, and more particularly to a fluorescence spectroscopy system and method having increased output detection sensitivity.

BACKGROUND

Fluorescent spectroscopy is a well-known technique used to characterize test specimens which may be biological or chemical test specimens. In general, the technique consists of illuminating the test specimen with light of a known wavelength. Molecules of the specimen absorb the light and subsequently fluoresce, which is to say emit light having a wavelength different than that of the absorbed light. In particular, the wavelength of the emitted light is longer than that of the excitation wavelength (absorbed light).

The observed or detected emission spectra (light intensity as a function of wavelength), which is referred to as the fluorescence emission spectra, provides detailed information on the structure and bonding characteristics of the molecules of the test specimen. This information can be used, in turn, to characterize and identify the material(s) of the specimen with a high degree of specificity.

In at least one geometry disclosed in the prior art for fluorescence spectroscopy, the fluorescence emission spectrum is generated and measured by applying an electric field to the walls of a containing tube while the sample specimen is in the tube. Typically, the electric field is applied using a pair of electrodes in close proximity to the tube. With this particular approach, the optical excitation, and the emission detection, occur from the "side" of the tube, i.e. transverse to the applied electric field (and to the general length of the tube). There are, however, problems with this approach.

When applying an electric field to the "sides" of the tube, the maximum electric field that can be applied to the test specimen is restricted and limited by the width or diameter of the tube and the dielectric strength (one measure of which is the maximum breakdown voltage) of the material used for the tube walls. Even in those instances where it is possible to impart an electric field substantially parallel to the direction of illumination (through the use of transparent electrodes), the relatively small widths of the container tube restrict the volume of test material excited by the illumination. The sensitivity and accuracy of the test method/device are therefore significantly reduced by the limited volume of material illuminated/tested.

Further, with most if not all of the fluorescent spectroscopy test systems disclosed in the prior art, a single set of electrodes is used, and the electric field is often applied as a static, constant field. While adequate for many simple test needs and small sample volumes, these approaches do not provide the flexibility to vary the electric field either spatially, or as a function of time. Similarly, larger volumes of test material cannot be sampled and evaluated.

In yet another geometry found in the prior art, liquid samples are contained within a flexible tube that is in turn coiled about a structure, such as a cylinder, in which is placed a reflector. Light is presented transverse to the flexible tube so as to excite the samples within the tube. The reflector will reflect light passing through or between the coils of the flexible tube back towards the coiled flexible tube. Any resulting fluorescence induced within the liquid sample is transferred by an optical fiber to a remote spectrometer. Fluid flow through the flexible tube is generally required and the length of the tube must not exceed certain lengths.

In addition, as the fluid is excited in one location and the florescence of the fluid measured in at a physically separate and somewhat distant location, loss of florescence is an undeniable issue. Further, fluorescence, such as it may be found, is measured entirely from the blunt cross section end of the flexible tube which may be quite small.

Hence, there is a need for a fluorescent spectroscopy system that overcomes one or more of the drawbacks identified above.

SUMMARY

The present disclosure advances the art by providing a system and method of detecting and quantifying light emitted from a test specimen, to characterize the specimen.

In particular and by way of example only, according to an embodiment provided is an optical measurement system including: a container structured and arranged to contain a specimen having one or more optical properties to be measured, the container having a first end and a second end and a length there between; a plurality of electrode pairs structured and arranged along the length of the container; a light source optically coupled to the first end of the container to illuminate the specimen from the first end along the length of the container; and a detector operable to detect emissions from the specimen indicative of the one or more optical properties.

DETAILED DESCRIPTION

Before proceeding with the detailed description, it is to be appreciated that the present teaching is by way of example, not by limitation. The concepts herein are not limited to use or application with a specific system for fluorescence spectroscopy. Thus, although the instrumentalities described herein are for the convenience of explanation, shown and described with respect to exemplary embodiments, it will be appreciated that the principles herein may be equally applied in other types of fluorescence spectroscopy systems.

Figure 1:
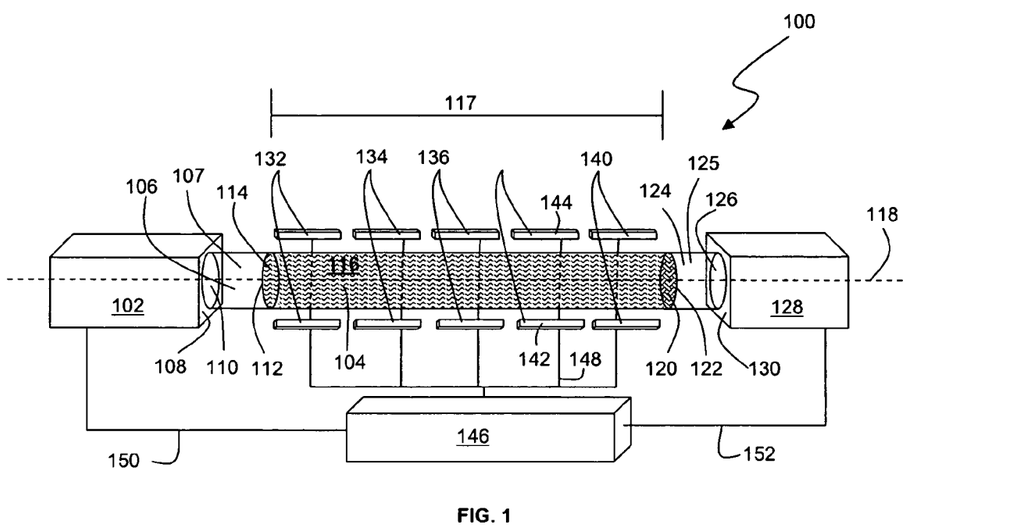
FIG. 1 is a perspective view of a fluorescence spectroscopy system, according to an embodiment.

FIG. 1 conceptually illustrates a fluorescence spectroscopy system 100 for characterizing biological and chemical materials and specimens having measurable optical properties, according to an embodiment. As shown, system 100 includes a light source 102 coupled to a container 116 containing a specimen 104. A plurality of electrode pairs 132, 134, 136, 138, 140 are arranged about container 116. A detector 128 is optically coupled to the container opposite from the light source 102.

As is further described below, it is to be appreciated that the light provided by light source 102 travels through the specimen 104 from the first end 114 of the container 116 to the second end 120 of the container 116. Moreover the light inducing florescence from the specimen 104 is not presented transverse to the specimen 104, or more specifically the container 116, but rather is presented so as to travel along the longitudinal axis 118 of container 116, and thus travel through the entire specimen 104 for the length of the container 116. This advantageous configuration will now be described in greater detail.

More specifically, as shown in FIG. 1, system 100 includes a light source 102 for providing light necessary to illuminate a test sample or material specimen 104 to be characterized. In at least one embodiment, specimen 104 is a fluid. Moreover, in at least one embodiment, specimen 104 is suspended in a liquid or fluid so as to provide a specimen in fluid form.

Light source 102 may be any of a type well-known in the art. In at least one embodiment, light source 102 is a polarized light source. The performance parameters of light source 102, to include the wavelength or wavelength band of the light transmitted by light source 102, are defined and known. In at least one embodiment, light source 102 is capable of operating as a ultra-violet (UV) light source.

In at least one embodiment, optically coupled to light source 102 is a light guide 106, which may be an optical fibre. In at least one embodiment, the core 107 of light guide 106 is formed of generally optically clear material such as plastic or plastic-type material, including but not limited to plastic such as acrylic, Plexiglas, polystyrene, polycarbonate material and combinations thereof. In an alternative embodiment, core 107 is formed of generally optically clear glass. The core 107 has an index of refraction, "n1", and a cladding (not shown) surrounding core 107 has an index of refraction, "n2", wherein n1>n2. Light guide 106 is preferably substantially totally internally reflecting ("TIR"), as discussed in greater detail below.

Still referring to FIG. 1, light source 102 may be joined to light guide 106 by means well known in the art. In at least one embodiment, light source 102 is joined to light guide 106 with a substantially boundary-less union at each interface using a glue that has an index of refraction substantially equal to that of the output surface 108 of light source 102 and core material 107 of light guide 106.

One end 110 of light guide 106 interfaces with an output surface 108 of light source 102. A second end 112 of light guide 106 interfaces with (and is optically coupled to) a first end 114 of a container 116, the container 116 encapsulating the material specimen 104 to be tested. Of note, container 116 may be any of a number of containers capable of containing material specimen 104, in whatever state it may assume (i.e. solid, fluid or gaseous). In particular, container 116 may be a chamber, capillary, cavity, pipe, tube, etc.

In at least one embodiment, material specimen 104 may be completely contained and stagnant within container 116, which is to say substantially motionless relative to an axis 118 and the walls, etc. of container 116. In at least one alternative embodiment, material specimen 104 may be moving or flowing through container 116, fir example along axis 118. In at least one embodiment, container 116 includes one or more ports (not shown) through which material specimen 104 may flow to enter and/or exit container 116. Generally, one port would be located adjacent to first end 112 and a second port would be located adjacent to second end 120. The distinction of which serves as an input port and which serves as an output port is a matter of preference to the system operator. As the measurement of florescence is performed with respect to the container 116, the length of flow to and from the container 116 may be largely immaterial.

Figure 2:
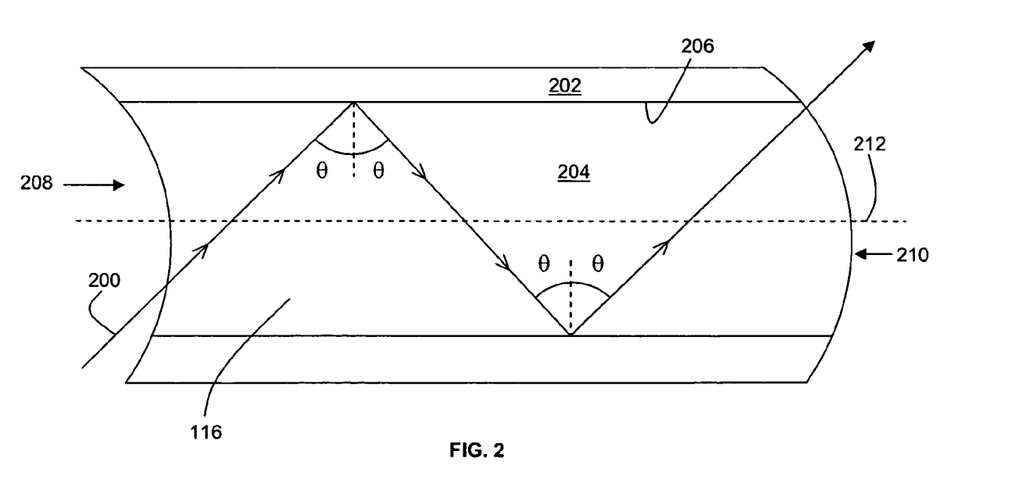
FIG. 2 is an enlarged section of a material specimen container, according to an embodiment.

Referring now to FIG. 2, an enlarged view of a section of container 116 is provided to further illustrate the possible TIR propagation of a light ray 200 through container 116. Of note, container 116 may be TIR by virtue of any one of several techniques well-known in the art, to include but not limited to: the addition of special additive materials to the test specimen, the use of specific geometries for container 116, index of refraction matching between the input end 114 of container 116 and the material of the test specimen, etc.

In at least one embodiment, a cladding 202 surrounds a cavity 204 of container 116, such that a boundary, e.g. boundary 206, is established between the cavity 204 and the cladding 202. In this configuration, container 116 may be totally internally reflecting ("TIR"). TIR occurs when a light ray (e.g. light ray 200) is both in a medium of higher index of refraction and approaches a medium of lower index of refraction, and the angle of incidence for the light ray is greater than the "critical angle." In particular, a light 200 received at an input end 208 is substantially delivered to an output end 210 with minimal loss.

The critical angle is defined as the smallest angle of incidence measured with respect to a line normal to the boundary between two optical media for which light is refracted at an exit angle of 90 degrees (that is, the light propagates along the boundary) when the light impinges on the boundary from the side of the higher index of refraction. For any angle of incidence greater than the critical angle, the light traveling through the medium with a higher index of refraction will undergo total internal reflection. The value of the critical angle depends upon the combination of materials present on each side of the boundary.

Light ray 200 travels through container 116 through successive TIR, as shown in FIG. 2. The angle of incidence and reflection off boundary 206 remains unchanged at angle "θ" until such time as light ray 200 is delivered to the output end 210. With a TIR container, such as container 116, the spread of light to either side of longitudinal centerline 212 is typically about thirty degrees (30°). Light exiting output end 210 will continue substantially in the direction last suggested by longitudinal centerline 212 unless reflected or refracted at output end 210.

While FIG. 2 depicts a single light ray 200 propagating along the length of container 116, it can be appreciated that multiple rays are transmitted from light source 102 into container 116 at any given moment in time. Each ray travels a path similar to that of light ray 200, until such time as the light exits container 116.

Returning now to FIG. 1, in at least one embodiment a second end 120 of container 116 is optically coupled to an end 122 of yet another light guide 124. In at least one embodiment, light guide 124 is an optical fiber, i.e. a fiber optic. Light guide 124 is structured and arranged to receive and transport light emissions exiting end 120 of container 116, as discussed in further detail below.

As with light guide or fiber optic 104, light guide 124 (which is to say the core 125 of light guide 124) is formed of generally optically clear plastic or plastic-type material, including but not limited to plastic such as acrylic, Plexiglas, polystyrene, polycarbonate material and combinations thereof. In an alternative embodiment, the core of light guide 124 is formed of generally optically clear glass. Light guide 124 may be TIR as well.

Still referring to FIG. 1, a second end 126 of light guide 124 interfaces with a detector 128 for detecting light emissions exiting container 116. More specifically, end 126 is optically coupled to input surface 130 of detector 128. Detector 128 may be joined to light guide 124 by means well known in the art. In at least one embodiment, detector 128 is joined to light guide 124 with a substantially boundary-less union at each interface using a glue that has an index of refraction substantially equal to that of the input surface 130 of detector 128 and the core material 125 of light guide 124. Detector 128 may be any of a type well-known in the art for detecting and/or recording light emissions in varying wavelength bands and bandwidths.

It can be appreciated by the skilled artisan that light guides 104 and 124 serve as a medium for transporting light either into (light guide 104) or out of (light guide 124) container 116. In at least one embodiment, the use of light guides is eliminated. In this instance, light source 102 and detector 128 are optically coupled directly to container 116.

Although shown in a substantially linear arrangement in FIG. 1, it can be appreciated that container 116, light guides 106, 124, light source 102 and detector 128 may be positioned, relative to each other, in any number arrangements from linear to non-linear, so long as the optical coupling between components is maintained. For example, container 116 and/or light guides 106, 124 may be flexible instead of rigid. As such, the position of one or more components of system 100, relative to one another and relative to axis 118, may vary if container 116 and/or light guides 106, 124 are bent or curved.

Oriented substantially parallel to the axis 118 defined by container 116 are one or more electrode pairs, of which electrode pairs 132, 134, 136, 138 and 140 are exemplary. In one embodiment, the electrodes of each electrode pair 132-140 are transparent. As shown, electrode pairs 132-140 may extend for substantially the length of container 116. In at least one embodiment, each electrode of an electrode pair 132-140, e.g. electrode 142 or 144, is positioned circumferentially about container 116. Alternatively, when container 116 is rectangular, or some other defined geometric shape, each electrode is positioned on a surface or face opposite that of its paired electrode. Regardless, each electrode pair 132-140 is structured and arranged to generate, when activated, an electric field through container 116, as shown for example in FIG. 3. As is illustrated, it is appreciated that the electrode pairs 132, 134, 136, 138 and 140 do not interfere with the delivery of light from the light source 102 to the specimen 104 within the container 116.

Of note, an electric field generated by each electrode pair (e.g. electric field 300 in FIG. 3), may be a static field. Stated differently, the field may be constant with respect to intensity, spatial position and time along the length of container 116. Alternatively, the field may vary spatially, and may be either static or varying with respect to intensity and time. Thus, the precise waveform of the electric field may be varying both spatially and temporally. The fluorescent signal from the sample will then exhibit similar frequencies in its expected response, and this will enable in the amplification of the signal and elimination of noise.

Figure 3:
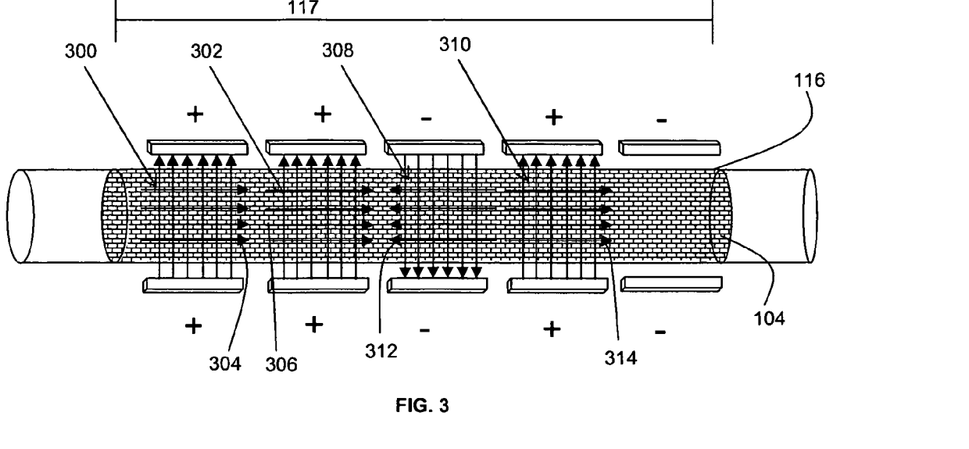
FIG. 3 is a perspective view of operational electrodes of a fluorescence spectroscopy system, according to an embodiment.

Electrode pairs 132-140 are electronically connected to a processor or controller, e.g. controller 146 in FIG. 1. For example, electrodes 142 and 144 of electrode pair 138 are connected to controller 146 via electronic cable 148. In this manner, controller 146 may provide to each electrode pair 132, 134, 136, 138 and 140 a current to generate the electric field of interest, e.g. electric field 300 (FIG. 3). As shown in FIG. 1, light source 102 and detector 128 may also be connected to controller 146 via electronic cables, such as cables 150 and 152 respectively.

As noted above, the electric fields generated by electrode pairs 132-140 may be static and constant, or they may vary as a function of space and time. Referring now to FIG. 3, electric fields 300 and 302 are representative of the fields generated, for example, by electrode pairs 132 and 134 (FIG. 1). As shown, the fields 300, 302 both have the same orientation (indicated by the "+" sign in proximity to each electrode). It can be appreciated that although the fields have the same orientation, they may be static i.e. constant with respect to time and intensity, or they vary as a function of time and intensity, while still maintaining a known (e.g. a "+") orientation.

In one embodiment of system 100, constant fields (e.g. "+" fields) are applied along the entire length of container 116. The molecules of specimen 104 align consistent with the fields, as represented by arrows 304 and 306. In yet another embodiment, the field(s) applied to specimen 104 may vary spatially, as exemplified by fields 308 and 310 (a "−" and "+" orientation respectively). In this instance, the orientation of the fields 308, 310 changes along the length of container 116. Stated differently, field 308 has an orientation opposite that of field 310, as represented by arrows 312 and 314, and the alternating "−" and "+" signs. As before, the molecules of specimen 104 tend to align consistent with the orientation of the electric fields (e.g. fields 308 and 310) acting on the molecules.

In at least one embodiment, the orientation of the electric fields may alternate along the entire length of container 116. In yet another alternative embodiment, the fields may vary and change as a function of time and intensity, while maintaining a constant orientation. Alternatively, the fields may change orientations as a function of time. The flow of current, as dictated by controller 146 (FIG. 1), controls the orientation, intensity, etc. of the electric fields 300, 302, 308 and 310. It can be appreciated that by varying the field(s) applied to the test specimen (e.g. specimen 104), the output emissions will vary as well. By knowing the electric field distribution, and therefore the orientation of specimen molecules and the point of emission for any given fluorescent ray of light, the characteristics of the material specimen may be further defined and refined. Thus, the precise waveform of the electric field may be varying both spatially and temporally. The fluorescent signal from the sample will then exhibit similar frequencies in its expected response, and this will enable in the amplification of the signal and elimination of noise.

Figure 4:
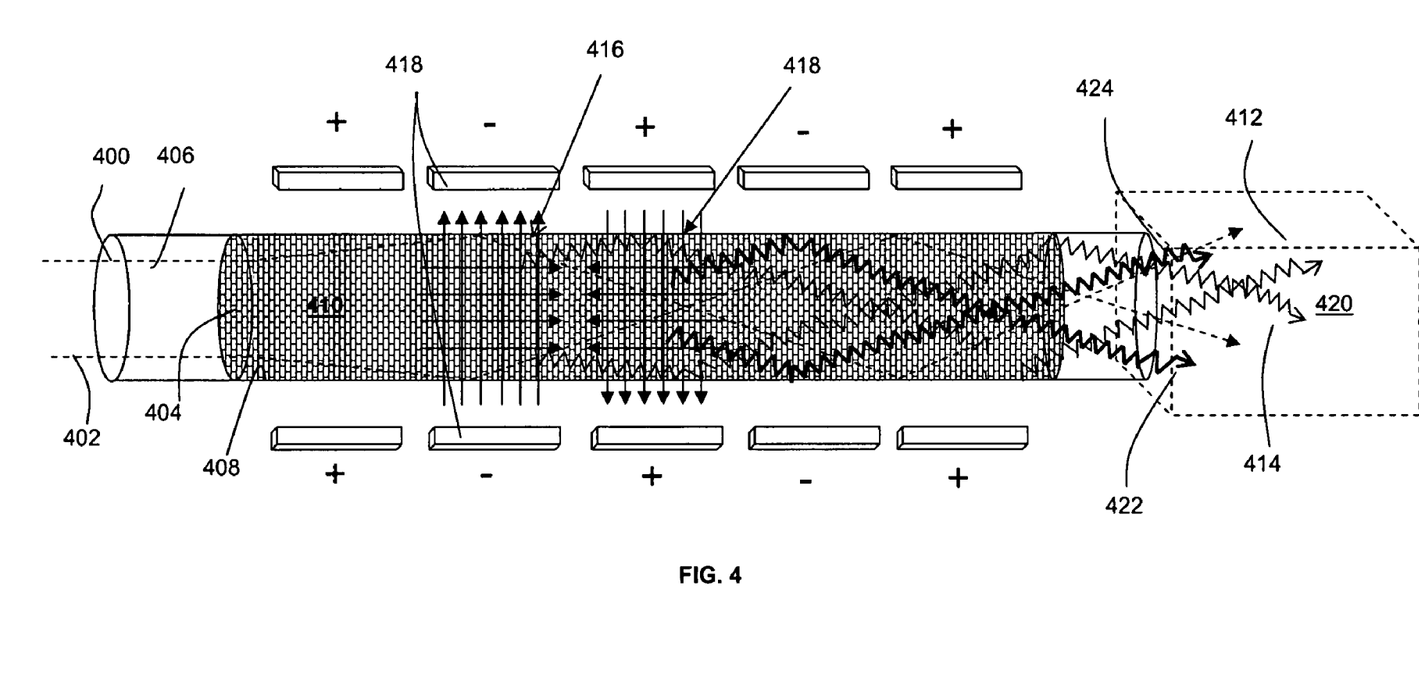
FIG. 4 is a perspective view of an operational fluorescence spectroscopy system with resulting fluorescence emissions, according to an embodiment.

In the operation of system 100, as shown in part by FIG. 4, rays of light having a known wavelength (e.g. rays 400 and 402) are directed toward a container 404 from a light source (not shown). As noted above, light rays 400, 402 may be polarized light. As rays of light 400, 402 enter container 404, a slight refraction of the light occurs at the light guide 406 to container 404 interface. In this instance, container 404 is TIR as described above, therefore, light rays 400, 402 travel the length of container 404, reflecting off boundary 408 in the process.

As the light rays 400, 402 travel the length of container 404, the light illuminates the molecules of test specimen 410. Stated differently, projected light rays 400, 402 interact with, and are absorbed by, molecules of specimen 410. The absorption of light rays 400, 402 causes specimen 410 to fluoresce, thereby giving off fluorescent light waves such as light waves 412 and 414. The light waves 412, 414 have a wavelength different from (and longer than) light rays 400 and 402. This emission of light waves 412, 414 is referred to as the fluorescence emission spectrum or spectra for specimen 410.

Although only two emitted light waves 412, 414 are shown for simplicity in FIG. 4, it can be appreciated that a plurality of light rays may be emitted from a single test specimen 410, as light projected from a light source (e.g. light source 102 in FIG. 1) travels the length of the container 404. In addition, as described above, fields 300, 302, 308 and 310 applied along the length of the container 116, and transverse to the propagation of light through the specimen 104, advantageously permit system 100 to induce different florescent properties within specimen 104.

More specifically, concurrent with the fluorescence of specimen 410, one or more electric fields, e.g. field 416, is generated by an electrode pair, such as electrode pair 418. As the electric field(s) 416 act upon the molecules of specimen 410, the molecules align consistent with the orientation of the fields. The net result of the alignment and fluorescence of specimen 410 is the emission of waves of light, e.g. waves 412 and 414 that are discernible and distinct with regard to their luminescent characteristics. Light waves 412 and 414 can be detected by a detector 420 for processing and analyzing the optical properties of specimen 410.

Alternatively, an electric field 418 may be applied having an orientation (e.g. a "+" orientation) opposite that of one or more adjacent fields 416. As such, when molecules of specimen 410 absorb light from rays 402 and 404, the emitted light rays 422 and 424 will have characteristics different from that of light emitted under the effects of field 416. These varying characteristics may be used to further define and classify the test specimen 410.

Stated differently, by detecting, quantifying and analyzing the fluorescence emission spectra, it is possible to define numerous characteristics of test specimen 410. It can be appreciated that by alternating or varying the electric fields applied to specimen 410, the resulting fluorescence emission spectra vary as well, yielding yet additional useful information.

In summary, a larger volume of test material or specimen is illuminated by projecting light along the length of a container (e.g. container 116). Further, each section of test specimen having a different molecular orientation (induced by varied electric fields) yields a different, yet beneficial, set of data to be analyzed.

Figure 5:
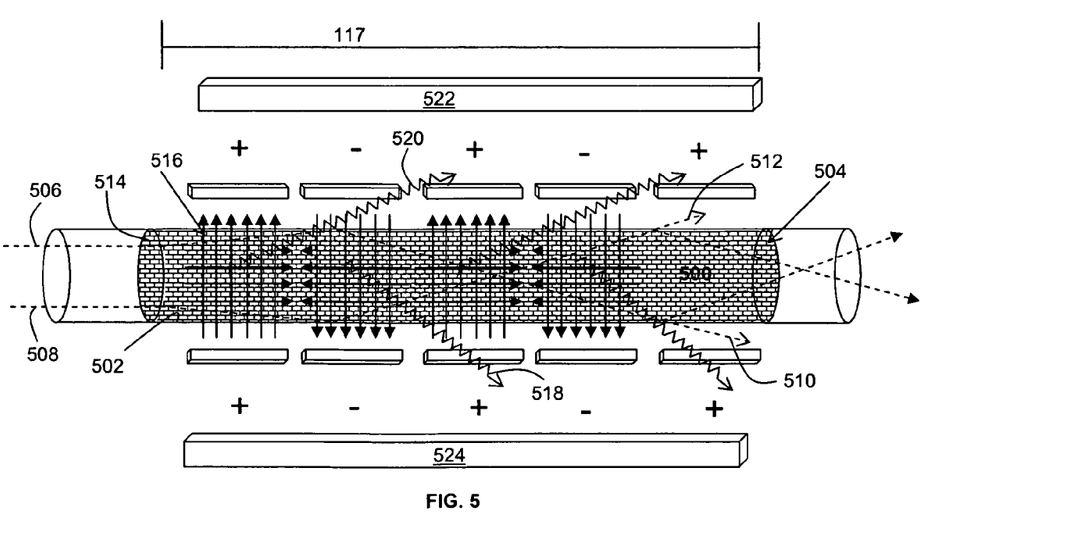
FIG. 5 is a perspective view of an operational fluorescence spectroscopy system with resulting fluorescence emissions, according to an embodiment.

In an alternate embodiment of system 100, as shown in FIG. 5, a container 500 may not be TIR. In this instance, some percentage of light striking boundary 502 will be transmitted through the boundary 502, and will not therefore exit the end 504 of container 502. For example, some portion of input light rays 506 and 508 will transmit through boundary 502, as represented by light rays 510 and 512.

The same will be true for light waves resulting from the fluorescence of specimen 514. As shown in FIG. 5, when specimen 514 interacts with light rays 506 and 508 in the presence of an electric field 516, resulting fluorescent light waves 518 and 520 are emitted. These waves 518, 520 may also exit through boundary 502.

In the configuration of FIG. 5, it may not be desirable to detect emitted waves 518, 520 of the fluorescence emission spectrum with a detector located in close proximity to the end 504 of container 502. In this embodiment, therefore, one or more detectors, of which detectors 522 and 524 are exemplary, may be used to detect emissions anywhere along the length of container 500. System 100 is advantageously capable of detecting these fluorescent light waves because of the relationship between the light source 102, the container 502, and the detectors 522, 524. As with the TIR containers of FIGS. 3 and 4, the emitted light waves (e.g. waves 518, 520) can be used to characterize a test specimen, and can vary with variations in electric field orientations, intensity, location, timing, etc. (The size and shape of the electrodes is most likely the same; ie, 132/134/136/etc. are similar. But it is possible to adjust geometries to get the signal out in the FIG. 5 configuration. Please reword as you see fit.)

Figure 6:
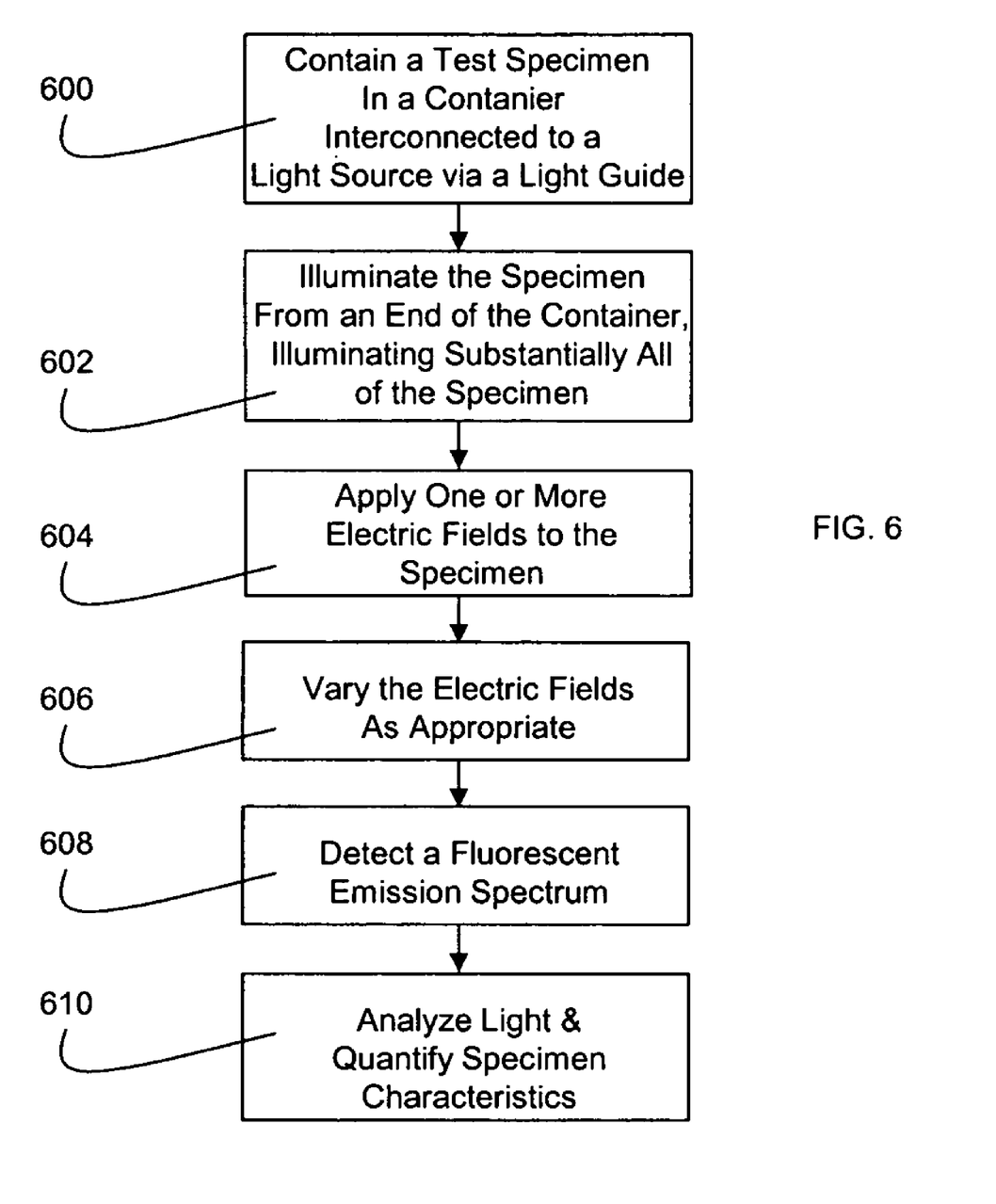
FIG. 6 is a method for measuring the fluorescent response of a test sample, to characterize the sample, according to an embodiment.

A summary method for characterizing biological and chemical materials and specimens by detecting and quantifying a fluorescent emissions spectrum is presented in FIG. 6. As a first step, a test specimen to be characterized is contained within a container which may or may not be TIR, block 600. The container may be interconnected to a light source via a fiber optic or other light guide, and the light source may be a polarized light source.

The specimen is illuminated from one end using light projected from the light source, block 602. In this manner, substantially all of the volume of the specimen is illuminated along the entire length of the container. The net result being a larger volume of illuminated test specimen from which to sample data. Concurrent with the illumination of the test specimen, one or more electric fields are applied to the specimen, block 604. The fields may be static and constant along the length of the container. Alternatively, the fields may vary (in orientation and/or intensity) spatially and as a function of time, block 606.

As discussed in detail above, illumination of the specimen will cause the molecules of the specimen to absorb the projected light, and consequently emit light (fluorescent light) having a wavelength longer than that of the projected light. The emitted light waves, which constitute a fluorescence emission spectrum, can be detected in one of several locations, block 608.

In particular, if the container is TIR, a detector may be interconnected to one end of the container via a fiber optic. In yet another embodiment, if the container is not TIR, one or more detectors may be positioned along the length of the container to collect emitted light. The detector is in electronic communication with a processor, and transmits data to the processor for analysis. In a final step in the process, the optical properties of the emitted light is quantified and analyzed (block 610), and characteristic details about the test specimen and its chemical/biological make-up are defined.

Changes may be made in the above methods, systems and structures without departing from the scope thereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

What is claimed is:

1. An optical measurement system, comprising:
   a container structured and arranged to contain a specimen having one or more optical properties to be measured, the container having a first end and a second end and a length there between;
   a plurality of electrode pairs structured and arranged along the length of the container, the electrical pairs operable to provide at least one oriented field transverse to the length to align molecules of the specimen disposed within the container;
   a light source optically coupled to the first end of the container to illuminate the specimen from the first end along the length of the container; and a detector optically coupled to the container, the detector operable to detect emissions from the specimen indicative of the one or more optical properties.

2. The optical measurement system of claim 1, further comprising an optical fiber having a first end optically coupled to the light source and a second end optically coupled to the first end of the container, for communicating light from the light source to the container.

3. The optical measurement system of claim 2, further comprising an optical fiber having a first end optically coupled to the second end of the container, and a second end optically coupled to the detector, for communicating emissions from the second end of the container to the detector.

4. The optical measurement system of claim 1, wherein the container exhibits total internal reflection.

5. The optical measurement system of claim 1, wherein the plurality of electrodes are operable to apply at least one electric field transverse to the propagation of light from the first end of the container along the length of the container.

6. The optical measurement system of claim 1, wherein the plurality of electrode pairs apply an electric field in a predetermined direction relative to the container, and further wherein the electric field is a static field.

7. The optical measurement system of claim 1, wherein the plurality of electrode pairs apply an electric field in a predetermined direction relative to the container, and further wherein the electric field is a varying field.

8. The optical measurement system of claim 1, wherein the light source is a polarized light source.

9. The optical measurement system of claim 1, wherein the one or more optical properties measured is an observed spectra of emitted light.

10. The optical measurement system of claim 1, wherein the plurality of electrode pairs are transparent.

11. An optical measurement system, comprising:
a container structured and arranged to contain a specimen having one or more optical properties to be measured, the container having a first end and a second end and a length there between;
a first optical fiber having a first and second end, the first end optically coupled to the first end of the container;
a light source optically coupled to the second end of the first optical fiber, the first optical fiber communicating light from the light source to the first end of the container to illuminate the specimen from the first end along the length of the container;
a second optical fiber having a first and second end, the first end optically coupled to the second end of the container;
a detector optically coupled to the second end of the second optical fiber, the detector operable to detect emissions from the specimen indicative of the one or more optical properties; and
a plurality of electrode pairs structured and arranged along the length of the container, the electrode pairs operable to provide at least one electric field transverse to the propagation of light from the first end of the container along the length of the container.

12. The optical measurement system of claim 11, wherein the electric field is a static field.

13. The optical measurement system of claim 11, wherein the electric field is a spatially varying field along the length of the containing means.

14. The optical measurement system of claim 11, wherein the electric field varies as a function of time.

15. An optical measurement system, comprising:
a containing means for containing a fluid having one or more optical properties to be measured, the containing means having a first end, a second end, and a length there between;
an electric field applying means for transversely applying an oriented electric field in a predetermined direction relative to the containing means, the oriented electric field aligning molecules within the fluid when disposed within the containing means;
an illumination means, optically coupled to the first end of the containing means, for illuminating the fluid within the containing means, the fluid illuminated along the length of the containing means between the first end to the second end; and
a detection means operable to detect emissions from the fluid, representative of the one or more optical properties, wherein the detection means is positioned to detect emissions from the second end of the containing means, the containing means exhibiting total internal reflection.

16. The optical measurement system of claim 15, further comprising an optical fiber having a first end optically coupled to the second end of the containing means, and a second end optically coupled to the detection means, for communicating emissions from the containing means to the detection means.

17. An optical measurement system, comprising:
a containing means for containing a fluid having one or more optical properties to be measured, the containing means having a first end, a second end, and a length there between;
an electric field applying means for transversely applying an oriented electric field in a predetermined direction relative to the containing means, the oriented electric field aligning molecules within the fluid when disposed within the containing means, wherein the applying means is a plurality of electrode pairs structured and arranged along the length of the containing means, a first electrode in each electrode pair positioned opposite a second electrode in the pairs;
an illumination means, optically coupled to the first end of the containing means, for illuminating the fluid within the containing means, the fluid illuminated along the length of the containing means between the first end to the second end; and
a detection means operable to detect emissions from the fluid, representative of the one or more optical properties.

18. The optical measurement system of claim 17, wherein each electrode pair has a polarity opposite that of an adjacent electrode pair.

19. The optical measurement system of claim 17, wherein the first and the second electrodes are transparent.

20. The optical measurement system of claim 17, wherein the containing means is a cylindrical tube, and further wherein the first and the second electrodes in each pair are positioned circumferentially about the tube.

21. An optical measurement system, comprising:
a containing means for containing a fluid having one or more optical properties to be measured, the containing means having a first end, a second end, and a length there between;
an electric field applying means for transversely applying an oriented electric field in a predetermined direction relative to the containing means, the oriented electric field aligning molecules within the fluid when disposed within the containing means;

an illumination means, optically coupled to the first end of the containing means, for illuminating the fluid within the containing means, the fluid illuminated along the length of the containing means between the first end to the second end, wherein the illumination means is a polarized light; and a detection means operable to detect emissions from the fluid, representative of the one or more optical properties.

22. A method for measuring one or more optical properties of a specimen fluid in a container, the container having a first end, a second end and a length there between, comprising:

applying an electric field transversely to the fluid in a predetermined direction relative to the container, the molecules of the specimen aligning with the field;

illuminating the fluid, from the first end along the length of the container between the first end and the second end, to influence the fluid to emit light indicative of the one or more optical properties;

detecting the emitted light;

analyzing the emitted light to quantify the one or more optical properties; and detecting the emitted light at the second end of the container, the container exhibiting total internal reflection.

23. The method of claim 22, further comprising applying a spatially varying electric field to the container.

24. The method of claim 23, wherein the spatially varying electric field is time varying.

25. The method of claim 22, further comprising detecting emitted light along the length of the container.

26. A method for measuring one or more optical properties of a specimen fluid in a container, the container having a first end, a second end and a length there between, comprising:

applying an electric field transversely to the fluid in a predetermined direction relative to the container, the molecules of the specimen aligning with the field;

illuminating the fluid, from the first end along the length of the container between the first end and the second end, to influence the fluid to emit light indicative of the one or more optical properties wherein illuminating further comprises using a polarized light source to illuminate the fluid;

detecting the emitted light; and analyzing the emitted light to quantify the one or more optical properties.

* * * * *